United States Patent
Chan et al.

(10) Patent No.: US 11,786,636 B2
(45) Date of Patent: Oct. 17, 2023

(54) METHODS FOR COMPLEX TISSUE ENGINEERING

(75) Inventors: Barbara Pui Chan, Hong Kong (HK); Hiu Wa Cheng, Hong Kong (HK); Daniel Tsz Kit Chik, Hong Kong (HK); Kenneth Man Chee Cheung, Hong Kong (HK); Keith Dip Kei Luk, Hong Kong (HK)

(73) Assignee: VERSITECH LIMITED, Hong Kong (CN)

( * ) Notice: Subject to any disclaimer, the term of this patent is extended or adjusted under 35 U.S.C. 154(b) by 1720 days.

(21) Appl. No.: 13/159,837

(22) Filed: Jun. 14, 2011

(65) Prior Publication Data

US 2012/0148632 A1   Jun. 14, 2012

Related U.S. Application Data (60) Provisional application No. 61/354,869, filed on Jun. 15, 2010.

(51) Int. Cl.

| | |
|---|---|
| C12N 5/00 | (2006.01) |
| C12N 5/02 | (2006.01) |
| A61K 45/00 | (2006.01) |
| A61L 27/38 | (2006.01) |
| C12N 5/071 | (2010.01) |
| A61K 35/51 | (2015.01) |
| C12N 5/077 | (2010.01) |
| A61K 35/545 | (2015.01) |
| A61K 35/28 | (2015.01) |
| A01K 67/00 | (2006.01) |

(52) U.S. Cl.
CPC .......... *A61L 27/3891* (2013.01); *A61K 35/28* (2013.01); *A61K 35/51* (2013.01); *A61K 35/545* (2013.01); *A61L 27/3834* (2013.01); *C12N 5/0012* (2013.01); *C12N 5/0654* (2013.01); *C12N 5/0655* (2013.01); *C12N 5/0697* (2013.01); *C12N 2502/1311* (2013.01); *C12N 2502/1317* (2013.01); *C12N 2502/1358* (2013.01); *C12N 2527/00* (2013.01); *C12N 2533/54* (2013.01)

(58) Field of Classification Search
CPC ...... A61K 35/51; A61K 35/545; A61K 35/28; C12N 5/0655; C12N 5/0697; C12N 5/0654; C12N 5/0012; C12N 2502/1311; C12N 2502/1317; C12N 2502/1358; C12N 2527/00; C12N 2533/54; A61L 27/3891; A61L 27/3834
See application file for complete search history.

(56) References Cited

U.S. PATENT DOCUMENTS

| | | | | |
|---|---|---|---|---|
| 8,246,684 | B2 * | 8/2012 | Lee | A61F 2/4405 623/17.15 |
| 8,277,832 | B2 * | 10/2012 | Detamore et al. | |
| 9,044,335 | B2 * | 6/2015 | Bonassar | A61L 27/44 |
| 2005/0069572 | A1 * | 3/2005 | Williams | A61K 45/06 424/426 |
| 2006/0198865 | A1 * | 9/2006 | Freyman | A61L 27/3804 424/423 |
| 2007/0184033 | A1 * | 8/2007 | Sevrain | A61F 2/30756 424/93.7 |
| 2007/0224172 | A1 * | 9/2007 | Hendriks et al. | 424/93.7 |
| 2008/0031858 | A1 * | 2/2008 | Chan | C12N 5/0012 424/93.7 |
| 2010/0036492 | A1 * | 2/2010 | Hung | A61L 27/56 623/14.12 |
| 2012/0015003 | A1 * | 1/2012 | Gleeson | A61L 27/24 424/400 |

FOREIGN PATENT DOCUMENTS

| | | |
|---|---|---|
| CN | 101248172 | 8/2008 |
| CN | 101439204 | 5/2009 |
| CN | 101721748 | 6/2010 |
| WO | 2005025493 | 3/2005 |
| WO | 2006079854 | 8/2006 |

(Continued)

OTHER PUBLICATIONS

Verghese et Feb. 2010, Stem Cells 28:765-774.*
Richardson et al 2009, J. Cell. Physiol. 222:23-32.*
Anderson et al. 2005, The Spine Journal 5:297S-303S.*
Penolazzi et al (Feb. 2010, Tissue Engineering 16:141-155.*
Reichert et al 2009, Biomed. Mater. 4:1-11.*
Hamilton et al. Formation of a nucleus pulposus-cartilage endplate construct in vitro. Biomaterials 27:397-405, (Year: 2006).*
Ruan et al. Intervertebral disc transplantation in the treatment of degenerative spine disease: a preliminary study. The Lancet 369: 993-999, (Year: 2007).*

(Continued)

*Primary Examiner* — Quang Nguyen
(74) *Attorney, Agent, or Firm* — PABST PATENT GROUP LLP (57) ABSTRACT

A simple, highly flexible and scalable platform for making functional complex tissues with heterogeneity and irregularity is provided. The method includes combining undifferentiated cells, such as pluripotent or multipotent stem cells, with a biomaterial to make multiple undifferentiated or naïve subunits, exposing the undifferentiated or naïve subunits to different cell culture environments for induction of differentiation towards different lineages as required by that complex tissue, and combining the then functional subunits with or without the undifferentiated subunits. The differentiated subunits thus combined can be cultured under biological, chemical, and/or physical culture conditions suitable to fine-tune the structural and functional properties of the bioengineered complex tissue to form a bioengineered tissue graft that mimics the structural and functional characteristics of native complex tissue. The bioengineered tissue graft can then used to replace dysfunctional tissue.

17 Claims, 5 Drawing Sheets

(56) References Cited

FOREIGN PATENT DOCUMENTS

| WO | 2008075206 | 6/2008 | | |
|---|---|---|---|---|
| WO | WO-2008078157 A2 | * | 7/2008 | .............. A61P 19/00 |
| WO | 2009142770 | 11/2009 | | |

OTHER PUBLICATIONS

Yow et al. Collagen-based fibrous scaffold for spatial organization of encapsulated and seeded human mesenchymal stem cells. Biomaterials 30:1133-1142, (Year: 2009).*

Allan, et al., "Formation of biphasic constructs containing cartilage with a calcified zone interface", Tissue Eng., 13:167-177 (2007).

Augst, et al., "Effects of chondrogenic and osteogenic regulatory factors on composite constructs grown using human mesenchymal stem cells, silk scaffolds and bioreactors", J R Soc Interface, 5(25):929-39 (2008).

Barbosa, et al., "Improved and simple micro assay for sulfated glycosaminoglycans quantification in biological extracts and its use in skin and muscle tissue studies", Glycobiology, 13:647-653 (2003).

Bergeret-Galley, et al., "The value of a new filler material in corrective and cosmetic surgery: DermaLive and DermaDeep", Aesthetic Plast. Surg., 25(4):249-55 (2001).

Broom, et al., "A functional-morphological study of the tidemark region of articular cartilage maintained in a non-viable physiological condition", J Anat., 135(1):65-82 (1982).

Chan, et al., "Self-assembled collagen-human mesenchymal stem cell microspheres for regenerative medicine", Biomaterials, 28:4652-4666 (2007).

Chan, et al., "Mesenchymal stem cell-encapsulated collagen microspheres for bone tissue engineering", Tissue Eng Part C Methods, 16(2):225-35 (2010).

Cheng, et al., "Mesenchymal stem cell-encapsulated collagen microspheres for bone tissue engineering", Tissue Engineering Part C. 15(4):697-706 (2009).

Corcos, et al., "Multicenter randomized clinical trial comparing surgery and collagen injections for treatment of female stress urinary incontinence", Urology, 65(5):898-904 (2005).

Gao, et al., "Osteochondral defect repair by demineralized cortical bone matrix", Clin Orthop Relat Res., 427(Suppl):S62-6 (2004).

Huang, et al., "Osteochondral repair using the combination of fibroblast growth factor and amorphous calcium phosphate/poly(L-lactic acid) hybrid materials", Biomaterials, 2007; 28(20):13091-100 (2007).

Hue, et al., "In vitro chondrogenic differentiation of human mesenchymal stem cells in collagen microspheres: influence of cell seeding density and collagen concentration", Biomaterials, 29:3201-3212 (2008).

Jiang, et al., "Repair of porcine articular cartilage defect with a biphasic osteochondral composite", J Orthop Res., 25(10):1277-90 (2007).

Kandel, et al., "Repair of osteochondral defects with biphasic cartilage-calcium polyphosphate constructs in a sheep model", Biomaterials, 27(22):4120-31 (2006).

Keeney, et al., "The osteochondral junction and its repair via bi-phasic tissue engineering scaffolds", Tissue Eng Part B Rev., 15(1):55-73(2009).

Klein, et al., "Tissue engineering of stratified articular cartilage from chondrocyte subpopulations", Osteoarthritis Cartilage, 11(8):595-602 (2003).

Kreklau, et al., "Tissue engineering of biphasic joint cartilage transplant", Biomaterlais, 20(18):1743-9 (1999).

Le Blanc, et al., "Treatment of severe acute graft-versus-host disease with third party haploidentical mesenchymal stem cells", Lancet, 363(9419):1439-41 (2004).

Martin, et al., "Osteochondral tissue engineering", J. Biomech. 40(4):750-65 (2007).

Pittenger, et al., "Mesenchymal stem cells and their potential as cardiac therapeutics", Circ Res., 95(1):9-20 (2004).

Pittenger, et al., "Multilineage potential of adult human mesenchymal stem cells", Science, 284(5411):143-7 (1999).

Sherwood, et al., "A three-dimensional osteochondral composite scaffold for articular cartilage repair", Biomaterials, 23(24):4739-51 (2002).

Shimizu, et al., "Cell sheet engineering for myocardial tissue reconstruction", Biomaterials, 24(13):2309-16 (2003).

Tuli, et al., "Human mesenchymal progenitor cell-based tissue engineering of a single-unit osteochondral construct", Tissue Eng., 10:1169-1179 (2004).

Yang, et al., "Engineering orthopedic tissue interfaces", Tissue Eng Part B Rev., 15(2):127-41 (2009).

Yu, et al., "Composition of cartilagenous tissue with mineralized and non-mineralized zones formed in vitro", Biomaterials, 18:1425 (1997).

Cheng, et al., "In vitro generation of an osteochondral interface from mesenchymal stem cell-collagen microspheres", Biomaterial, 32:1526-35 (2011).

* cited by examiner

METHODS FOR COMPLEX TISSUE ENGINEERING

CROSS REFERENCE TO RELATED APPLICATIONS

This application claims benefit of U.S. Provisional Application No. 61/354,869, filed Jun. 15, 2010, which is hereby incorporated herein by reference in its entirety.

FIELD OF THE INVENTION

The present invention generally relates to bioengineered tissue. Specifically, it relates to methods for producing tissue grafts with more than one tissue component.

BACKGROUND OF THE INVENTION

Tissue dysfunction can be caused by traumatic, genetic or surgical reasons. For mild injuries, some tissues are able to regenerate on their own, while other tissues particularly those of hypovascular nature can hardly regenerate. Many attempts have been made to provide treatment options for tissue dysfunction, including growth factor therapy, cell therapy and gene therapy. However, these attempts are only useful when the extent of tissue dysfunction is not massive. When the tissue dysfunction is massive, replacement therapy via a surgical approach is necessary. In this regard, tissue engineering approaches for growing and culturing three-dimensional (3D) tissue-like structures made of cells and biomaterial-based scaffolds, supplemented with growth stimulating signals offer great hope for tissue replacement therapies.

In the last two decades, tremendous advances in biomaterial and fabrication technologies, stem cell technologies and bioreactor technologies have been made, making it easier to make 3D tissue-like structures with structural and functional similarities to native tissues for replacement purposes. Nevertheless, all organs are made of complex tissues with more than one tissue component having distinct structures, cell types and functions. Complex tissues are tissues or organs with more than one tissue components. On the other hand most, if not all functional tissues are made of more than one component, and have distinct structures and cell type. Examples of complex tissues include: an osteochondral graft, which consists of bone and cartilage with an organized calcified cartilage zone; a spinal motion segment, which consists of a pair of bone blocks interfacing with a pair of thin cartilaginous endplates sandwiching an intervertebral disc with annulus fibrosus encapsulating nucleus pulposus; and a ligament bone graft, which consists of two bony blocks interfacing a ligamentous strips in the middle. The inherent heterogeneity of complex tissues renders complex tissue engineering or engineering of organs made up of the complex tissues, a challenge in the field.

Bioengineering complex tissues is extremely challenging because (1) multiple cell types for different tissue components are needed, making the sourcing problem complicated; (2) multiple biological and stable tissue interfaces are required, in view of the critical functions played by the tissue interfaces in assuring the normal function of the complex tissues; (3) maintenance of multiple phenotypes and functions is needed, making the culture conditions complicated; and (4) numerous irregularities in morphological, structural and functional properties of different tissue components and their interfaces are present in complex tissues but are difficult to mimic.

Providing multiple parenchymal cell types for different tissue components of a complex tissue is almost clinically impossible. This is because multiple biopsies from different tissue components of a healthy tissue counterpart are too invasive, and cells in the dysfunctional tissue are usually abnormal. Further, mature cells have limited life span and proliferative potential. Pluripotent stem cells able to differentiate towards all phenotypes of different tissue components of the complex tissue being engineered provide solutions to this problem. However, most existing attempts to bioengineer complex tissues involve the use of either multiple cell sources, making clinical applications difficult, or, combinations of stem cells and mature cells isolated from different sources, a very complicated solution.

Biological and functional tissue interfaces, e.g., osteochondral interface, are important features of complex tissues. Only recently has the significance of interface tissue engineering begun to receive increasing attention (Broom, et al., *J Anat.*, 135(1):65-82 (1982).; Yang, et al., *Tissue Eng Part B Rev.* 2009; 15(2):127-41 (2009); Keeney, et al., *Tissue Eng Part B Rev.*, 15(1):55-73(2009)). Prior approaches include fabricating scaffolds for osteo-part and chondro-part separately before combining them, using solid-free-form fabrication technology to build scaffolds with heterogenicity (e.g., gradient porosity), and encapsulating cells directly in hydrogels before combining using photopolymerization (Sherwood, et al., *Biomaterials*, 23(24): 4739-51 (2002); Alhadlaq, et al., *J. Bone Joint Surg Am.*, 87(5):936-44 (2005)). Nevertheless, the results are far from reaching the ultimate goal of simulating the structural zonal organization and achieving the functional mechanical properties of the native osteochondral interface, and many challenges remain to be tackled (Broom, et al., *J Anat.*, 135(1): 65-82 (1982); Yang, et al., *Tissue Eng Part B Rev.*, 15(2): 127-41(2009); and Keeney, et al., *Tissue Eng Part B Rev.*, 15(1):55-73 (2009)).

First, the optimal combination of cells and scaffolds remains to be defined. Bioceramics such as hydroxyapatite are the most popular choice for the osteo-part or bone aspect, while synthetic polymers such as poly-lactic-co-glycolic acid (PLGA) are commonly used for the chondro-part or cartilage aspect (Kreklau, et al., *Biomaterials*, 20(18): 1743-9 (1999); Gao, et al., *Clin Orthop Relat Res.*, 427 (Suppl): 562-6 (2004); Huang, et al., Biomaterials. 2007; 28(20):3091-100 (2007); and Jiang, et al., *J Orthop Res.*, 25(10):1277-90 (2007). Chondrocytes isolated from different zones behave differently and have the potential to engineer cartilage tissues with biomimetic zonal organization (Klein, et al., *Osteoarthritis Cartilage*, 11(8):595-602 (2003). For example, chondrocytes from the deep zone of articular cartilage have been cultured in calcium phosphate, which acts as the scaffold for the osteo-part and, in the absence of a counterpart scaffold for the chondro-part, these cells resulted in formation of a calcified zone in vitro (Yu, et al., *Biomaterials*, 18:1425 (1997); Allan, et al., *Tissue Eng.*, 13:167-177 (2007); Kandel, et al., *Biomaterials*, 27(22): 4120-31 (2006)). The clinical availability of these cells would likely be problematic due to: (i) the need to harvest biopsies from non-load bearing regions, and (ii) limited proliferation potential of chondrocytes in vitro.

Multipotent and pluripotent stem cells, such as bone marrow derived mesenchymal stem cells (MSCs), are promising because of their self-renewal capability and multiple differentiating potential (Pittenger, et al., *Science*, 284 (5411):143-7 (1999); Pittenger, et al., *Circ Res.*, 95(1):9-20 (2004); and Le Blanc, et al., *Lancet*, 363(9419):1439-41 (2004)). Despite the promise of MSC, in studies using MSCs and silk scaffolds (Augst, et al., *J R Soc Interface*, 5(25): 929-39, (2008), or MSC and poly-D,L-lactic acid scaffolds (Tuli, et al., *Tissue Eng.*, 10:1169-1179 (2004), no calcified zone was observed despite the persistent contact of the cartilage-like part with the bone-like part. In the Tuli studies, although the composite was cultured in culture medium which is able to maintain chondrogenic and osteogenic phenotypes simultaneously, the culture conditions could not support the formation of a calcified cartilage interface (Tuli, et al., *Tissue Eng*, 10:1169-1179 (2004)).

Secondly, integration with the host cartilage is a common problem to most existing strategies, as multiple cylindrical plugs are usually used to fill defects. These plugs are usually irregularly shaped, leading to limited integration and increased contact pressures due to nonuniformity in the articular surfaces (Yang, et al., *Tissue Eng Part B Rev.*, 15(2):127-41 (2009); Keeney, et al., *Tissue Eng Part B Rev.*, 15(1):55-73 (2009); Martin, et al., *J. Biomech.* 40(4):750-65 (2007)). Cell sheet technology, which includes laminating multiple confluent monolayers of cells, seems to be a flexible and scalable technology able to make tissues with heterogeneity (Shimizu, et al., *Biomaterials*, 24(13):2309-16 (2003)). However, multiple laminations take time because adhesion of one layer to the previous layer is time-consuming. The time of open surgery is consequently very long. As a result, only thin layer tissues with high cellularity such as epithelial and endothelial tissues can be made using this method. Tissues with bulk matrices, tissues requiring mesenchymal cell types, tissues with load-bearing functions, and with irregular tissue interfaces, etc, cannot be made using this approach.

Therefore, bioengineering a complex tissue with heterogeneity and irregularity requires a more flexible and scalable technology, which allows the formation and maintenance of multiple tissue types with multiple stable tissue interfaces from simple cell and material sources, with better efficacies and lower costs.

It is therefore an object of the invention to provide flexible and scalable methods of producing complex tissues which are made up of more than one tissue component.

It is also an object of the invention to provide methods for repairing complex tissue defects by implanting the complex tissue scaffolds disclosed herein at a site in need of complex tissue replacement.

SUMMARY OF THE INVENTION

A simple, highly flexible and scalable platform for making functional complex tissues with heterogeneity and irregularity is described. A representative method using the platform involves combining pluripotent or multipotent cells, such as stem cells, with a biomaterial to make multiple undifferentiated or naïve subunits. In some embodiments, these undifferentiated or naïve subunits are microencapsulated pluripotent or multipotent cells. The method further involves exposing at least part of the undifferentiated or naïve subunits to different environments for induction of differentiation towards different lineages as required by that complex tissue, and combining the then functional subunits with or without the undifferentiated or naïve subunits to form the bioengineered complex tissue which mimics the native complex tissue in terms of the structural irregularity and heterogeneity. In some embodiments the undifferentiated or naïve subunits are further induced to differentiate by exposing the undifferentiated pluripotent or multipotent cells to appropriate microenvironment including but not limited to differentiation culture media and mechanical loading, which are able to maintain the multiple phenotypes in the bioengineered complex tissues. In other embodiments the undifferentiated pluripotent or multipotent cells are induced to differentiate by interactions with multiple differentiated progenies of the stem cells.

Also provided is a method of making a bioengineered tissue graft that involves combining two or more functional subunits, optionally separated by undifferentiated encapsulated pluripotent or multipotent cells, wherein each of the two or more functional units are encapsulated pluripotent or multipotent cells induced to differentiate into different cell types; and culturing the combined functional units to form a bioengineered tissue graft that mimics the structural and functional characteristics of a complex tissue.

Suitable pluripotent or multipotent cells for use in cell engraftment include induced pluripotent stem cells, embryonic stem cells, fetal stem cells, cord blood stem cells, bone marrow derived stem cells, and adipose tissue derived stem cells.

The pluripotent or multipotent cells are encapsulated in a biomaterial barrier, such as an extracellular matrix biomaterial. In preferred embodiments, the extracellular matrix biomaterial is collagen. The cells can be encapsulated into any suitable structure, such a microsphere, cube, ring, or micro-rod.

In some embodiments, the encapsulated pluripotent or multipotent cells are induced to differentiate using any available means, such as chemical induction, genetic manipulation, or by reconstitution of the biological and mechanical microenvironment.

In some embodiments, the method further involves fine-tuning the structural and functional properties of the bioengineered tissue graft by exposing it to suitable biological, chemical, and physical co-culture conditions. In some embodiments, the combined functional units are cultured in the presence of conditioned medium, growth factors, cytokines, serum, and combinations thereof. In some embodiments, the combined functional units are cultured under chemical conditions suitable to promote functional and structural characteristics of the complex tissue. Chemical conditions include antioxidants, acids, alkali, oxygen tension, and combinations thereof. In some embodiments, the combined functional units are cultured in the presence of forces selected from the group consisting of torsion, compression, tension, and combinations thereof.

Complex tissues relevant to the disclosed methods include osteochondral tissue, intervertebral discs, spinal motion segments; ligament bone tissue, cardiac strip with cardiac muscle containing vascularized networks, growth plate with highly organized hierarchical layers of cartilage with bony tissues able to lengthening and thickening, and a liver patch with hepatocytes fully vascularized. In preferred embodiments, the complex tissue is osteochondral tissue having zonal organization. In other embodiments, the complex tissue is a spinal motion segment having a multi-lamella structure of the annulus fibrosus.

Another embodiment provides a method of repairing a tissue defect that involves administering the disclosed bioengineered tissue graft at a site of tissue damage in the subject. Another embodiment provides a method of repairing a tissue defect that involves implanting a combination of naïve and/or differentiated subunits at a site in need thereof.

In another embodiment, the combined naïve and differentiated subunits can be cultured under biological, chemical, and/or physical culture conditions suitable to fine-tune the structural and functional properties of the bioengineered complex tissue prior to implantation. Suitable biological culture conditions include custom-made culture medium, conditioned medium, growth factors and cytokines, serum and other blood products, and combinations thereof. Suitable chemical conditions include antioxidants, acids, alkali, oxygen tension, and combinations thereof. Suitable physical conditions include mechanical loading with forces selected from the group consisting of torsion, compression, tension, and combinations thereof.

Also provided is a method of producing a calcified zone interface in a bioengineered tissue construct that involves culturing a construct in vitro having first, second and third layers to induce a calcified zone between the first and third layers; wherein the first layer contains microencapsulated pluripotent or multipotent cells treated to induce osteogenic differentiation; wherein the second layer is adjacent to the first layer and separates the first and third layers and contains undifferentiated microencapsulated pluripotent or multipotent cells; wherein the third layer is adjacent to the second layer and contains pluripotent or multipotent cells treated to induce chrondogenic differentiation.

Also provided is a method of producing a complex tissue construct that involves culturing two layers of encapsulated stem cells induced to differentiate joined together by a layer of undifferentiated encapsulated stem cells under conditions to induce the formation of a complex tissue construct.

Also provided is a bioengineered tissue graft produced by the disclosed methods.

Also provided is a bioengineered osteochondral tissue construct comprising first, second and third layers, wherein the first layer contains microencapsulated pluripotent or multipotent cells treated to induce osteogenic differentiation, wherein the second layer is adjacent to the first layer and separates the first and third layers and contains undifferentiated microencapsulated pluripotent or multipotent cells; wherein the third layer is adjacent to the second layer and contains pluripotent or multipotent cells treated to induce chrondogenic differentiation. In preferred embodiments, the bioengineered construct has a calcified zone interface between the first and third layers.

Also provided is a method of treating osteochondral damage in a subject that involves administering to the subject the disclosed bioengineered osteochondral construct at the site of osteochondral damage.

Also provided is a method of producing a bioengineered spinal motion segment that involves inducing microencapsulated pluripotent or multipotent stem cells to form osteogenic subunits; combining the osteogenic subunits with microencapsulated pluripotent or multipotent stem cells induced to form chondrogenic subunits, wherein the combination of osteogenic subunits and chondrogenic subunits form bone blocks containing endplates; and sandwiching an intervertebral disc with annulus fibrosus encapsulating nucleus pulposus with the bone blocks containing endplates to form a spinal motion segment. The intervertebral disc can be natural, bioengineered, or synthetic.

DETAILED DESCRIPTION OF THE INVENTION

I. Definitions

As used herein, "complex tissue" refers to an aggregate of two or more cell types performing separate biological functions. Exemplary complex tissues include but is not limited to osteochondral tissue and organ tissue.

As used herein, "bioengineered complex tissue" and "bioengineered tissue graft" refer to a composition or structure that when implanted into complex tissue produces tissue that mimics the structure and function of the complex tissue.

As used herein, "undifferentiated or naïve subunits" are undifferentiated cell biomaterial subunits made by technologies such as microencapsulation.

As used herein, "functional subunits" are differentiated tissue micromasses, which claim the functions of the native tissues.

As used herein, "encapsulated in microspheres" refers to formation of a nanofibrous microsphere having embedded therein cells as a result of a phase change of the material forming the microsphere.

As used herein, "stem cell" refers generally to undifferentiated cells regardless of source, and includes multipotent cells, pluripotent cells, de-differentiated cells, embryonic stem cells, mesenchymal stem cells, and induced pluripotent stem cells. Stem cells can be embryonic or adult stem cells.

As used herein, "totipotency" refers to the ability of a single cell to divide and produce all the differentiated cells in an organism, including extraembryonic tissues.

As used herein, "pluripotency" refers to the ability of a single cell to differentiate into cells of any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent cells cannot develop into a fetal or adult animal because they lack the potential to contribute to extraembryonic tissue, such as the placenta.

As used herein, "multipotent" refers to cells that have the potential to differentiate into multiple cell lineages but not to cells of all three germ layers.

As used herein, "subject" refers to any individual who is the target of administration. The subject can be a vertebrate, for example, a mammal. Thus, the subject can be a human. The term does not denote a particular age or sex. A patient refers to a subject afflicted with a disease or disorder. The term "patient" includes human and veterinary subjects.

II. Method of Forming Complex Tissues

Figure 2:
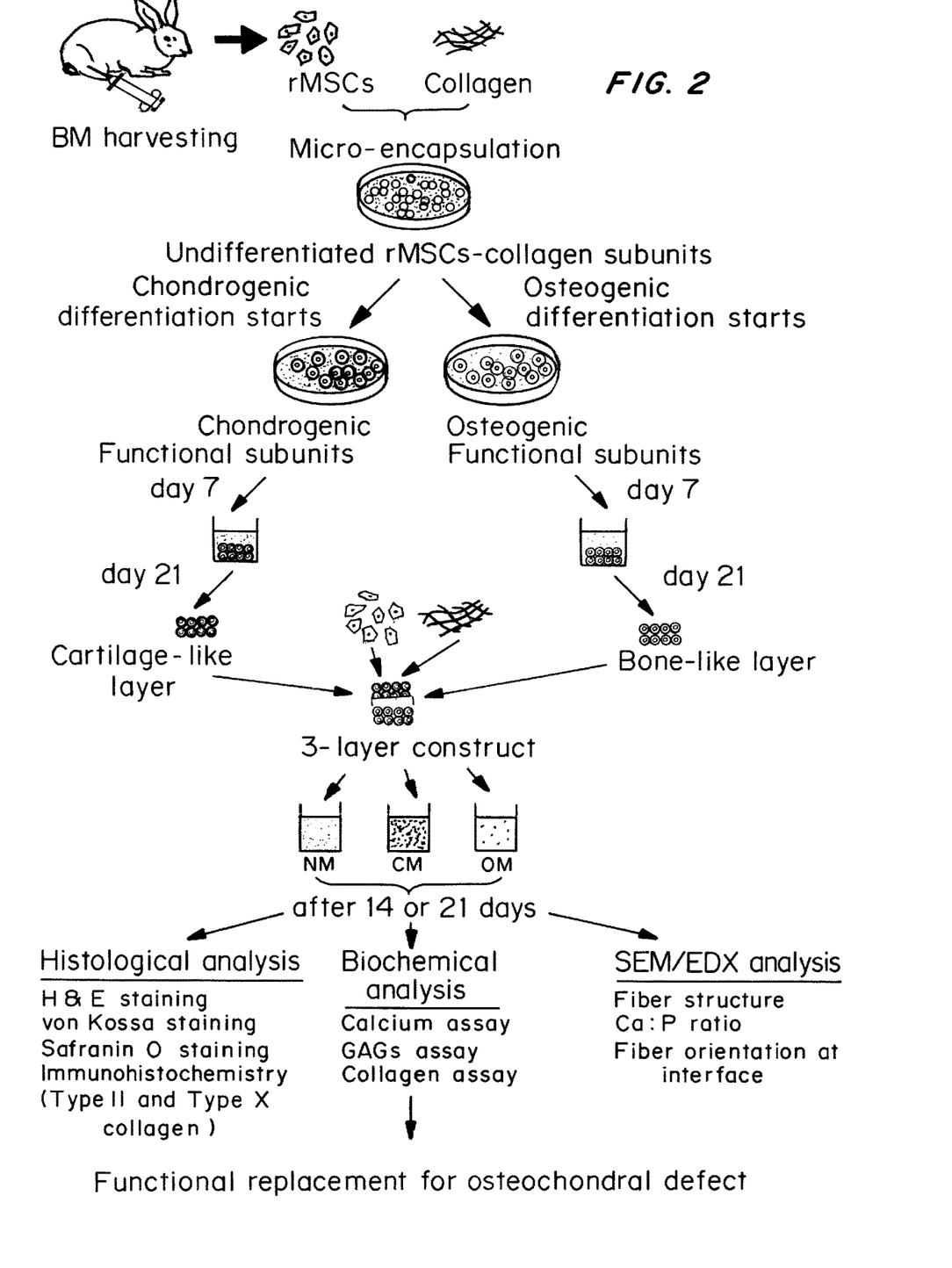
FIG. 2 is a flow diagram showing the method for making an osteochondral graft with bone and cartilage with a calcified cartilage interface, as an example for complex tissue engineering.

Bioengineering a complex tissue requires more flexible and scalable technologies allowing formation and maintenance of multiple tissue types with multiple stable tissue interfaces from simple cell and material sources. The disclosed methods make use of the concept that tissues are made of functional subunits, which are tissue micromasses with a small volume, such as $10^{-6}$ ml, and with cells ranging from say 100 to 1000. The disclosed methods also make use of the multiple differentiation potential of various types of stem cells, and the interactions between undifferentiated stem cells, differentiating stem cells, and their differentiated progenies. The disclosed methods further make use of the ability of cells to remodel their existing matrix, including but not limited to the extracellular matrix and microenvironment, for fine tuning differentiation of cells into the desired tissue structure. The remodeled matrix is formed from cells, preferably stem cells responding to various signals. Specifically, provided herein is a method to condition the bioengineered complex tissue in vitro by mimicking or reconstituting the biological and mechanical microenvironment of the tissue as much as possible, such that multiple cellular or tissue phenotypes can be maintained and functional complex tissues can be grown. The method integrates multiple functional subunits of different tissue components of the complex tissue so as to bioengineer a complex tissue. The examples demonstrate that the disclosed methods are efficient in making an osteochondral graft with calcified cartilage interface in 5 weeks, from a single stem cell source and a single biomaterial (FIG. 2). Its efficacy and simplicity make complex tissue engineering possible and affordable.

A. Cells

Representative cells useful in the disclose methods include, but are not limited to, pluripotent or multipotent cells, such as adult or embryonic stem cells, as the only cell source for making multiple tissue components of the complex tissues. The stem cells can be induced pluripotent cells (iPSCs) obtained via viral or non-viral methods, embryonic stem cells, fetal stem cells, cord blood stem cells, bone marrow derived stem cells such as mesenchymal stem cells (MSCs), and adipose tissue derived stem cells such as mesenchymal stem cells and the like. A clinically feasible stem cell source such as bone marrow derived mesenchymal stem cells is preferred as it can be easily obtained and is more ethically and socially acceptable.

B. Extracellular Matrix (ECM) Biomaterials

The composition includes at least one biomaterial, which must be capable of providing support to the cells, interacting with the cells to allow cell growth without introducing toxicity, and permitting cell migration and penetration. The biomaterial can be collagen of different types, such as type I, II, and III, or any materials that are good in supporting cell growth and migration and have phase transition properties at conditions mild enough to support cell survival, such as fibrin and hyaluronic acid. The collagen used can be of bovine origin such as those used in United States Food and Drug Administration (FDA)-approved skin equivalents Integra® and Apligraf® and the soft tissue fillers or products that have been used clinically for wrinkle reduction such as DermaLive® and DermaDeep® (Bergeret-Galley, et al., *Aesthetic Plast. Surg.*, 25(4):249-55 (2001), or for urinary incontinence treatment (Corcos, et al., *Urology*, 65(5):898-904 (2005)). The biomaterial can be derived from either natural or synthetic sources, and it can be induced to reconstitute into solid form under specific conditions that are mild enough to support cellular survival and growth. The biomaterial can be produced from isolation or extraction from various animal sources, such as rat tail, porcine skin, bovine Achilles tendon, or human placenta. Preferably, the biomaterial is isolated from different fractions during the extraction process, such as acid-soluble, pepsin-soluble, or insoluble fractions.

The composition can further include a second biomaterial, which can be a proteoglycan or glycosaminoglycan ("GAG") obtained from shark cartilage, fibrin, elastin or hyaluronic acid. The first biomaterial can interact with living cells or with the second biomaterial in such a way that the interaction leads to a change in cellular responses in growth and differentiation and physical properties of microspheres such as the volume of the structures, biomaterial density, cell density, mechanical property and stability, etc.

Suitable biomaterials also include hydrogels whose fabrication conditions are mild enough to maintain high cell viability after encapsulation without the use of organic solvents or other substances toxic to cells, and without harsh conditions, such as alginate gel which is gelled by addition of calcium.

The biomaterials do not affect the stem cell nature of the multipotent or pluripotent cells. It presents an optimal scaffold to allow remodeling of the biomaterial into a native tissue like matrix by the differentiating cells, and support new tissue component or tissue interface growth in the complex tissue engineering process. The biomaterials can be both synthetic, natural, or a combination thereof. Preferred biomaterials include, but are not limited to biomaterials able to self-assemble into a fibrous meshwork entrapping the stem cells before the stem cells differentiate into cells of different progenies or lineages. The biomaterials include but are not limited to collagen, fibrinogen, elastin, self-assembling peptides, and combinations thereof.

C. Complex Tissue Formation

Undifferentiated cells, e.g., stem cells, are combined with a biomaterial to form a complex tissue. In one embodiment, the cell/biomaterial combination is converted into numerous undifferentiated or naïve subunits using microencapsulation. The microencapsulation does not affect the stem cell nature of the undifferentiated cells. Preferred methods of microencapsulation include but are not limited to the method described in U.S. Published Application No. 2008/0031858 by Chan, et al. or described in Chan, et al., *Biomaterials*, 28:4652-4666 (2007), both of which are incorporated by reference in their entireties where permissible. Microencapsulation enables the undifferentiated cells to be entrapped in a micron-sized biomaterial structure, for example a microsphere, a cube, or a micro-rod, with controllable size, without affecting the stem cell nature, which includes the self-renewal capacity and the multiple differentiation potential of the stem cells [Chan, et al., *Biomaterials*, 28:4652-4666 (2007)). These micron-sized biomaterial structures or subunits can be used for subsequent differentiation or combination to form the complex tissues.

The naïve subunits are differentiated into different lineages or progenies corresponding to the different tissue components in the complex tissues using methods known in the art, which include but are not limited to, chemical induction, reconstituting the biological microenvironment and genetic manipulation. The naïve subunits thus treated become functional subunits, i.e., are differentiated tissue micromasses, which have the biological functions of the native tissues. Examples include cartilage-like micromasses, which are made by chondrogenic differentiation of the naïve MSC-collagen microspheres, and bone-like micromasses by osteogenic differentiating the native MSC-collagen microspheres (Table 1).

TABLE 1

Mean values with standard deviations (SDs) for the relative composition of calcium and phosphorus in different groups.

|  | Ca (weight %) | P (weight %) | Ca/P (Molar ratio) |
|---|---|---|---|
| Chondrogenic layer (Mean ± SD) | 1.09 ± 0.92 | 0.69 ± 0.55 | NA |
| Interface (Mean ± SD) | 4.38 ± 3.04 | 2.70 ± 1.59 | 1.199 ± 0.133 |
| Osteogenic layer (Mean ± SD) | 31.67 ± 4.88 | 17.07 ± 2.19 | 1.431 ± 0.056 |

The functional subunits contain remodeled scaffolds and differentiated progenies of the stem cells. For example, cartilage-like functional subunits can be formed from the naïve subunits using methods described in Hue, et al., *Biomaterials*, 29:3201-3212 (2008), and bone-like functional subunits can be formed from the naïve subunits using methods described in Chan, et al., *Tissue Eng Part C Methods*, 16(2):225-35 (2010). Following differentiation of the functional subunits, the functional subunits are combined to form a complex tissue-like structure. In some embodiments, functional subunits of the same cell type are combined prior to combining with the functional subunits of another cell type. In one embodiment, the subunits are combined in a random manner by mixing different subunits in suspensions before co-culturing the subunits at high subunit density. In another embodiment, the subunits are combined in a predetermined pattern by integrating the subunits in appropriate configurations simulating that of the heterogeneity and irregularity of the native tissues. This can be done at appropriate time points with appropriate configurations. The duration for combination should also be optimal depending on different complex tissues. Different complex tissues have different designs and the bottom line is to mimic the native tissue structures as much as possible.

In other embodiments the disclosed methods make use of the direct or indirect interactions between the differentiated progenies of the stem cells and the undifferentiated stem cells in appropriate configurations and conditions, such that the differentiated progenies also induce the undifferentiated stem cells to differentiate towards a lineage that is difficult to induce simply by chemical induction. Differentiated progenies of stem cells are differentiated cells, early or late during the differentiation pathway, obtained from the undifferentiated stem cell source by many different methods including known chemical induction protocol, known genetic manipulation protocol, and indirect induction methods when the differentiation protocol is unknown. If the differentiation protocol for chondrocytes is unknown for example, an indirect method is to entrap mature cells from easily obtained animal or human sources in biomaterials by microencapsulation, and allow the mature chondrocytes to grow and remodel the biomaterial scaffold into one that simulates the native tissue microenvironment, before discarding the mature cells and repopulating the subunits with undifferentiated stem cells. The matrix and biological environment reconstituted by the mature cells would induce the repopulated undifferentiated stem cells into chondrocyte-like cells, as differentiated progenies of the undifferentiated stem cells (Cheng, et al., *Tissue Engineering Part C.* 15(4): 697-706 (2009)).

Figure 1:
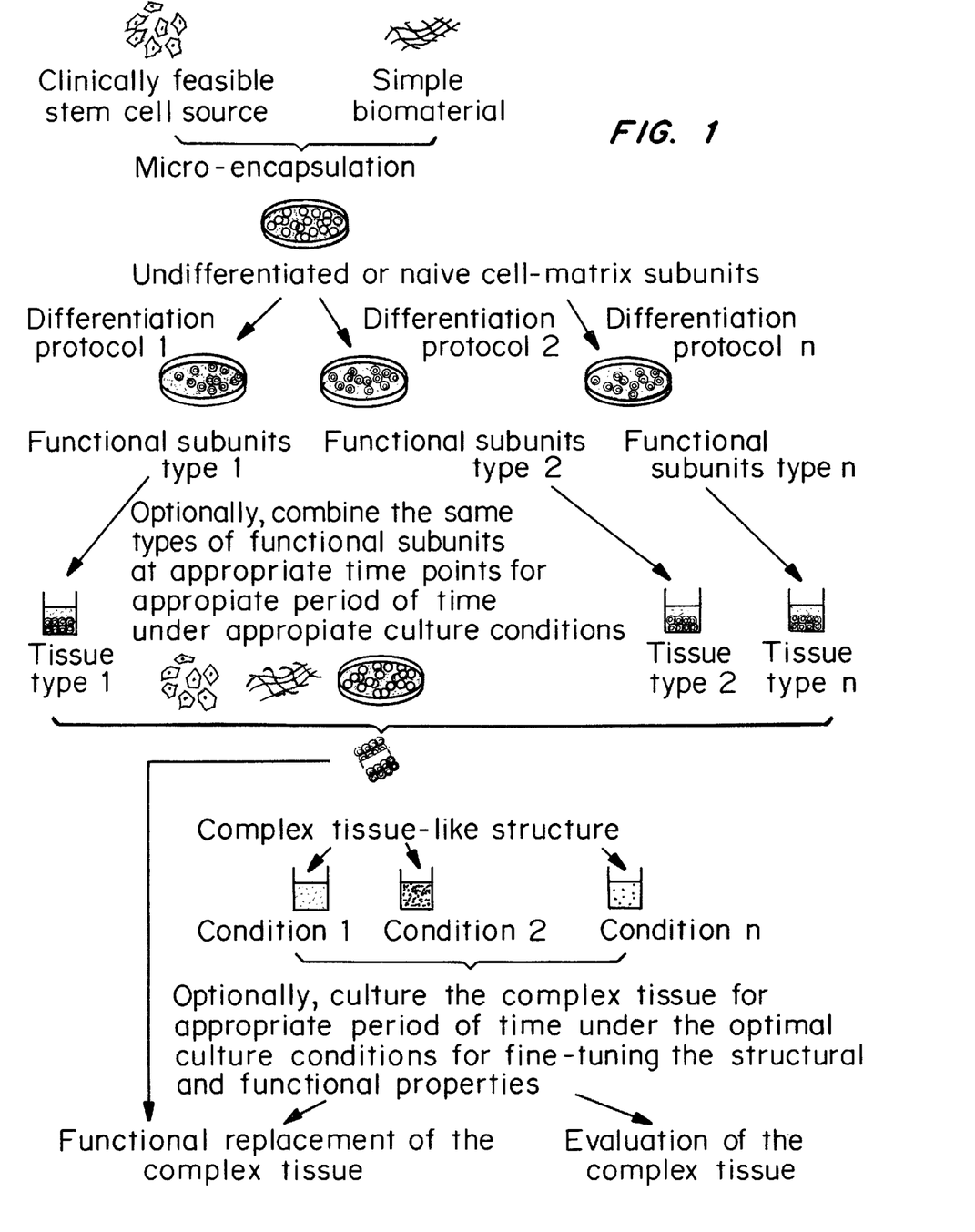
FIG. 1 is a flow diagram summarizing the method of complex tissue formation.

Interactions between differentiated progenies of the stem cells and their undifferentiated counterparts includes co-culture of the functional subunits with differentiated progenies of the stem cells with the naïve subunits made of undifferentiated stem cells under appropriate culture conditions with appropriate 3D configurations, for appropriate periods of time. Such interactions can be direct contact between the differentiated progenies and the undifferentiated stem cells, or indirect induction by secreted factors from the differentiated progenies. The interactions can also involve secreted factors from the differentiated stem cells. Such interactions can be used to induce the undifferentiated stem cells into a second or third or $n^{th}$ lineage or progeny that cannot be directly differentiated due to the unknown chemical differentiation protocol. For example, it is difficult to directly differentiate stem cells to form uncalcified cartilage and calcified cartilage cells (hypertrophic chondrocytes) simultaneously with proper zonal organization. It is possible to induce such zonal organization by properly configuring undifferentiated or native subunits with the functional subunits made of differentiated progenies, osteogenic and chondrogenic in this case. The undifferentiated stem cells are induced to differentiate into hypertrophic lineages constituting the calcified cartilage layer and this may be due to the secreted factors including but are not limiting to BMP2 by the differentiated progenies in the functional subunits The differentiated subunits combined as described above are used to replace the dysfunctional complex tissue. Alternatively, the differentiated subunits thus combined can be cultured for an appropriate period of time, under appropriate conditions for fine-tuning the structural and functional properties of the tissue. A schematic showing the method disclosed herein provided in FIG. 1.

The cells can be differentiated by altering or modifying biological culture conditions, chemical culture conditions, physical culture conditions, or combinations thereof. Biological conditions can be modified by including conditioned medium from other cells, co-culturing with other cells, including growth factors and cytokines, serum and other blood products, and combinations thereof. Chemical conditions can be modified by including antioxidants, acids, alkali, or modifying oxygen tension, etc. Physical conditions can be modified by changing mechanical loading with forces of different modes such as torsion, compression and tension or any combinations of these, with different extent and frequencies, and the like. Bioreactors can be used in which the biological, the chemical and the mechanical microenvironments of the cells can be customized and optimized for production of different complex tissues.

III. Complex Tissues

Examples of complex tissues that can be formed according to the methods described herein include an osteochondral graft, which consists of bone and cartilage with an organized calcified cartilage zone; a spinal motion segment, which consists of a pair of bone blocks interfacing with a pair of thin cartilaginous endplates sandwiching an intervertebral disc with annulus fibrosus encapsulating nucleus pulposus; a ligament bone graft, which consists of two bony blocks interfacing a ligamentous strips in the middle; a cardiac strip with cardiac muscle with vascularized networks; a growth plate with highly organized hierarchical layers of cartilage with bony tissues able to lengthening and thickening, and a liver patch with hepatocytes fully vascularized. A schematic for forming an osteochondral graft for example, is shown in FIG. 2.

Using a spinal motion segment as an example, naive microspheres are exposed to osteogenic differentiation conditions to form osteogenic subunits and then combined to form the bone blocks. Naive subunits are exposed to chondrogenic differentiation conditions to make chondrogenic subunits and then combined to form thin and large layers as the end-plates. Osteochondral interfaces between the bone block and the endplate can be formed using the same method as that illustrated in the osteochondral graft example—formation of a tri-layered construct with undifferentiated cells (e.g., MSCs) in the middle layer and co-cultured in the optimal co-culture medium such as chondrogenic medium in this case. Two such osteochondral units are used to form the spinal motion segment, where a middle disc-like part is combined again by multi-layer co-culture. The disc like part can be obtained by the method illustrated above when the differentiation protocol is unknown. The multilayered construct can be fit on a bioreactor providing mechanical loading simulating the native tissue for better integration of different tissues and continuous tissue growth before it is ready for implantation.

The present invention will be further understood by reference to the following non-limiting examples.

The present invention will be further understood by reference to the following non-limiting examples.

EXAMPLES

Example 1

Bone Marrow Aspiration and Rabbit Mesenchymal Stem Cell (rMSCs) Isolation

Three month old New Zealand white rabbits weighing an average of 3.5 kg were anesthetized by an intramuscular injection of a mixture of 10% ketamine hydrochloride (0.35 ml/kg) and 2% xylazine (0.25 ml/kg). Approximately 5 ml of bone marrow was aspirated from the tibia. After Ficoll-Hypague gradient separation, mononuclear cells at the interface were collected and cultured in Dulbecco's modified Eagle's medium (DMEM) containing 10% fetal bovine serum (FBS) and antibiotics. The medium was refreshed 10 days after seeding, and replenished every 2 days thereafter. Visible colonies of adhered cells were found about 5 to 7 days after the initial plating. After reaching confluence (about 12 to 14 days after initial plating), the cells were detached by 0.25% trypsin/EDTA for subculture.

Example 2

Culture of rMSCs rMSCs were cultured in full medium consisting of Dulbecco's modified Eagle's medium high glucose (DMEM-HG), 10% fetal bovine serum (FBS), 100 U/ml penicillin, 100 mg/ml streptomycin, 1.875 mg/ml sodium hydrogen carbonate ($NaHCO_3$), 0.02M HEPES, and 0.29 mg/ml L-glutamine. The final pH of the medium was adjusted to 7.4 with 1 N sodium hydroxide (NaOH). Live cells were separated from dead cells following 24 hours in cultures, by adherence selection i.e., the cells were cultured for 24 hours and then the adhered cells separated from the dead cells which would be in the culture medium. Cells were maintained in full medium, which was replenished every 3 days. rMSCs at subconfluence were detached by 0.25% trypsin/EDTA. Cells from passage 2-3 were used for the subsequent microencapsulation step.

Example 3

Fabrication of Naïve Subunits—Collagen-rMSCs Microspheres

Ice-cold rat tail collagen type I (Becton Dickenson) was neutralized with 1N NaOH and was further diluted with full medium to give a final concentration of 2 mg/ml. Aliquots of rMSCs at P2-P3 in full medium were rapidly mixed with the neutralized collagen solution in an ice bath, resulting in a cell-matrix mixture with a final cell density of 1250 cells/2.5 µl droplet. Liquid droplets were dispensed into a 35 mm-diameter Petri dish (Sterlin) with UV irradiated parafilm covering the substratum. After incubation at 37° C. in a humidified atmosphere with 5% $CO_2$ for 1 hour, the liquid droplets gelated to form solid rMSCs-collagen microspheres, which were then gently flushed into Petri dish using full medium and cultured for 3 days before the differentiation step.

Example 4

Formation of Cartilage-Like Functional Subunits

Chondrogenic differentiation of rMSCs-collagen microspheres was induced by culturing the rMSC-collagen microspheres as suspensions in chondrogenic differentiation induction medium 3 days after forming the naive subunits. Chondrogenic differentiation induction medium was defined as Dulbecco's modified Eagle's medium-high glucose (DMEM-HG), supplemented with 10 ng/ml recombinant human TGF-β1 (Merck, Darmstadt, Germany), 100 nM dexamethasone (Sigma), 0.1 mM L-ascorbic acid 2-phosphate (Fluka, St. Louis, Mo., USA), 6 µg/ml insulin (Merck), 6 µg/ml transferrin (Sigma), 1 mM sodium pyruvate (Gibco, Grand Island, N.Y., USA), 0.35 mM L-proline (Merck) and 1.25 mg/ml bovine serum albumin (BSA) (Sigma). Medium was regularly changed every 3 days for 3 weeks. At 7 and 21 days post-differentiation, around 10 microspheres were harvested and processed for histological evaluation including routine H&E staining, type II collagen immunohistochemistry and glycosaminoglycan (GAG) analysis, biochemical evaluation measuring the GAG/Hydroxyproline (HYP) ratio, and mechanical evaluation of the elastic modulus of the chondrogenic differentiated microspheres. These microspheres, which are the cartilage-like functional subunits were used subsequently for the integration and combination step for complex tissue engineering.

Figure 3A:
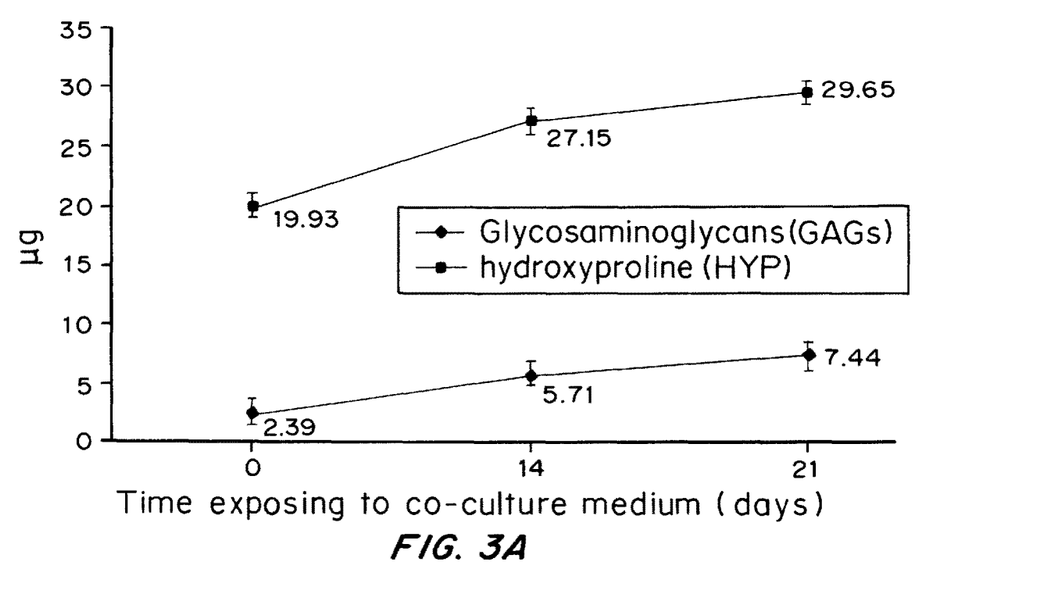
FIG. 3A is a line graph showing relative amounts (µg) of glycosaminoglygans (GAGs) (♦) and hydroxyproline (HYP) (■) in microspheres cultured in chondrogenic medium as a function of time (0, 14, and 21 days) (n=4).

The cartilage-like functional subunits stained positive with Alcian blue, indicating the presence of glycosaminoglycans and type II collagen. Although the GAG/HYP ratio was only 7% of the value for native cartilage, the composition and structure of the micromasses improved and the values increased to 12 and 15% of the native tissue when they are further cultured in the co-culture medium for 14 and 21 days, respectively (FIGS. 3A and 3B), suggesting that further remodeling in the co-culture medium was ongoing. Longer incubation and stimulation with further chondrogenic differentiation signals may be used.

Example 5

Fabrication of Bone-Like Functional Subunits

Osteogenic differentiation of rMSCs in collagen microspheres was induced by culturing the rMSC-collagen microspheres as suspensions in osteogenic differentiation induction medium 3 days after forming the naïve subunits. Osteogenic differentiation induction medium was defined as Dulbecco's modified Eagle's medium-low glucose (DMEM-LG), supplemented with 10% FBS, 100 nM dexamethasone (Sigma), 0.1 mM L-ascorbic acid 2-phosphate (Fluka, St. Louis, Mo., USA), and 10 mM β-glycerophosphate (Sigma).

Medium was regularly changed every 3 days for 3 weeks. At 7 and 21 days post-differentiation, around 10 microspheres were harvested and processed for histological evaluation including routine H&E staining, von Kossa staining, biochemical analysis on for total calcium content of the osteogenic differentiated microspheres.

Figure 3B:
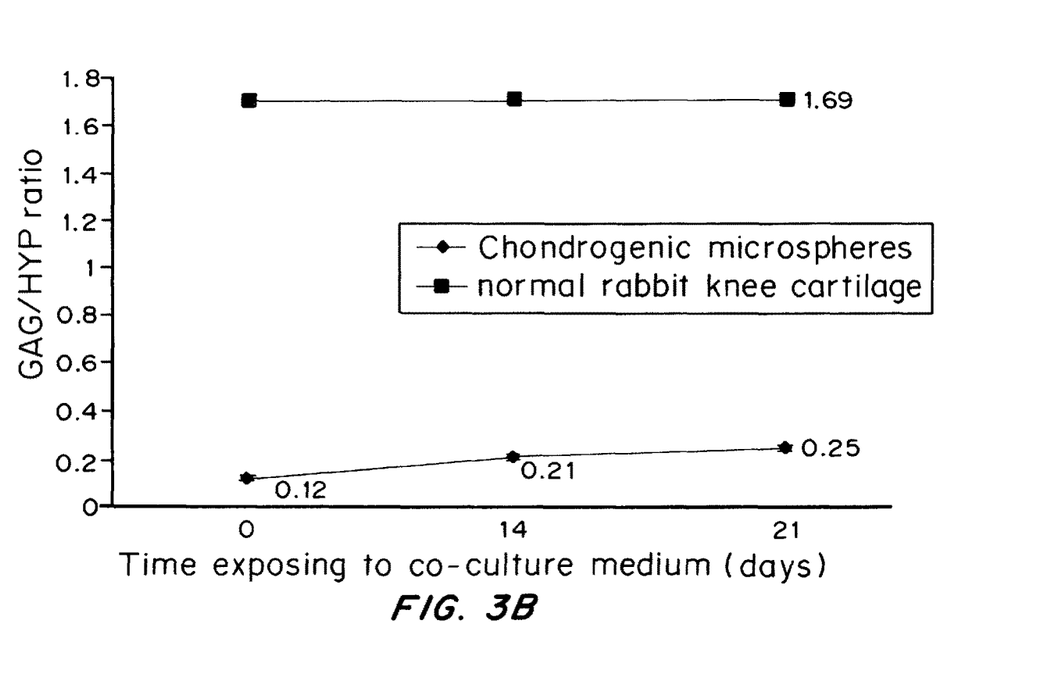
FIG. 3B is a line graph showing GAGs/HYP ratio in chondrogenic microspheres (♦) compared to normal rabbit knee cartilage (■) as a function of time (0, 14, and 21 days) (n=4).
Figure 3C:
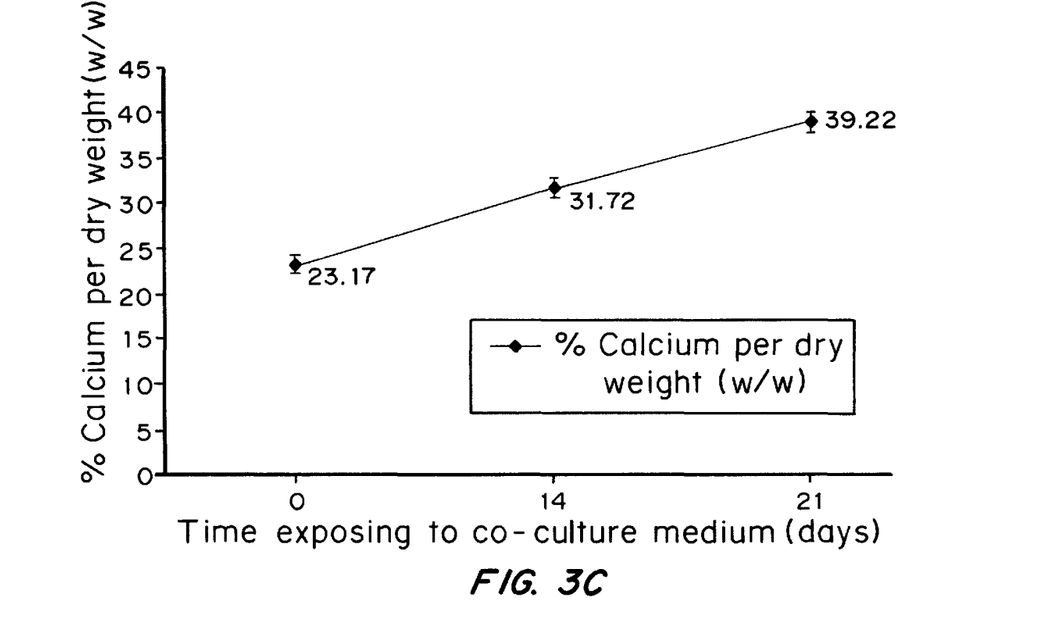
FIG. 3C is a line graph showing percentage calcium per dry weight (w/w %) in osteogenic microspheres as a function of time (0, 14, and 21 days) (n=5).

These bone-like functional subunits stained positive with von kossa staining Quantitative calcium content measurement showed that the calcium content reached more than 20% in the functional subunits (FIG. 3C). Calcium deposition continued to increase as co-culture time increased, indicating that the co-culture conditions maintained the osteogenic phenotype successfully. The co-culture included culturing the undifferentiated MSCs in a middle layer, which can also be the naive subunits, the osteogenic subunits and the chondrogenic subunits, all together, after combining into tri-layers with appropriate configuration.

Example 6

Quantitative Analysis of GAG/HYP Ratio of Cartilage-Like Microspheres

GAGs content was determined by the 1,9-dimethylmethylene blue dye-binding assay (Barbosa, et al., *Glycobiolog*, 13(9):647-53 (2003)). In brief, for each group, 80 microspheres per sample were placed in a phosphate buffer at pH 6.5 (50 mM phosphate buffer, 5 mM EDTA, and 5 mM L-cysteine) containing 300 µg/mL papain to solubilize the proteoglycans. Digestion was carried out at 60° C. overnight. Absorbance at 656 nm was then measured using a microplate reader (Safire 2™; Tecan, Mannedorf, Switzerland). The amount of GAGs in the samples was determined using a calibration curve prepared using chondroitin sulfate as a standard with a linear region between 0.5 and 2 µg/100 µL (Barbosa, et al., *Glycobiology*, 13:647-653 (2003).

Collagen content was determined by the Sircol collagen assay. In brief, for each group, 80 microspheres per sample were placed in a 0.5N acetic acid solution containing pepsin. Digestion was carried out at 4° C. overnight. Absorbance at 555 nm was then measured using a microplate reader (Safire 2™; Tecan, Mannedorf, Switzerland). The amount of collagen in the samples was determined using a calibration curve prepared by bovine collagen standard with a linear region between 6.25 and 25 µg/100 µL. The hydroxyproline content was taken to be 14% of total collagen content. The GAG/HYP ratio is shown in FIG. 3B. Example 7: Integration of different subunits for fabrication and co-culture of bi- and tri-layered osteochondral constructs Three hundred and sixty osteogenic differentiated collagen-rMSC microspheres were packed. An aliquot of 200 µl collagen gel at 2 mg/ml with undifferentiated rMSCs at $5 \times 10^5$ cells/ml was added as a middle layer immediately before packing three hundred and sixty chondrogenic differentiated collagen-rMSC microspheres as the upper layer. The tri-layered osteochondral constructs were then divided into 3 groups and cultured in either normal medium (NM), chondrogenic medium (CM), or osteogenic medium (OM) for another period of either 14 days or 21 days. Bi-layered constructs consisting of either the chondrogenic or the osteogenic part together with an undifferentiated rMSC-collagen gel layer were fabricated in a similar manner and used as controls. All co-cultured constructs were evaluated histologically and immunohistochemically, using GAGs and type II collagen as chondrogenic markers, calcium deposition as an osteogenic marker and type X collagen as the interface marker. The ultrastructure of the tri-layered constructs was also evaluated by scanning electron microscopy (SEM) and Energy Dispersive X-ray (EDX) analysis. Micromasses comprising the whole construct were still visible.

Example 8

Histological and Immunohistochemical Evaluation

Samples (whole construct after co-culture, either tri-layered or the bi-layered construct) were fixed in 4% paraformaldehyde (PFA), embedded in paraffin and cut into 7 µm sections. Hematoxylin and eosin (H&E) staining was used to show cell morphology, Safranin O staining was used to show GAG-rich regions, and immunohistochemistry against collagen type II and collagen type X was used as phenotypic markers for chondrocyte and hypertrophic chondrocyte respectively.

For collagen type II immunohistochemistry, sections were incubated with 0.5% pepsin in 5 mM HCl at 37° C. for 30 minutes for antigen retrieval. After overnight incubation at 4° C. with a mouse anti-type II collagen polyclonal antibody (Calbiochem) at a dilution of 1:2000 in PBS, sections were incubated with an anti-mouse secondary antibody at a dilution of 1:200 in PBS for 30 minutes at room temperature.

For immunohistochemistry against collagen type X, sections were incubated with 0.2% hyaluronidase in PBS at 37° C. for 1 h, and then with 0.1% pronase (in PBS) for 9 min for antigen retrieval. After overnight incubation at 4° C. with a mouse anti-type X collagen monoclonal antibody (Abcam) at a dilution of 1:2000 in normal horse serum, sections were incubated with an anti-mouse secondary antibody at a dilution of 1:800 in normal horse serum for 30 minutes at room temperature. The Vectastain ABC kit (Vector Laboratories) and the DAB substrate system (Dako) were used for color development in both cases according to the suppliers' instructions.

von Kossa staining was used to identify calcium deposits in the mineralized region. Briefly, sections were immersed in 1% silver nitrate solution (Sigma) under UV irradiation for 30 min. Un-reacted silver was removed by 2% sodium thiosulphate solution for 5 min. Nuclear Fast Red was used as the counterstain.

Proper zonal organization with calcified cartilage interface separating a bone-like and a cartilage-like layer was identified in the tri-layered configuration. Positive von kossa staining identified calcium deposition, positive type II collagen and positive Alcian blue staining was indicative of cartilage, and positive type X collagen was indicative of the hypertrophic nature of the tri-layered structures. In contrast, no such zonal organization could be identified in the bi-layered configuration (the control) or when the tri-layered configuration was constructed without an undifferentiated subunit in the middle layer. In the bi-layered controls, there was no middle layer; in the tri-layered control (i.e., cell-free tri-layered), plain collagen gel constituted the middle layer.

Example 9

Quantification of Calcium Content

In order to evaluate whether the osteogenic phenotype was maintained in chondrogenic differentiation medium during the tri-layer culture, calcium deposits from the osteogenic layer of the microspheres were extracted with 1% trichloroacetic acid for 24 hours and quantified using a calcium assay kit (Bioassay Systems, Hayward, Calif., Cat

: DICA-500). In brief, equal volumes of Reagent A and Reagent B were combined and equilibrated to room temperature before use. Standard solutions of $Ca^{2+}$ (12.5-200 µg/mL) were prepared by serial dilution in distilled water. An aliquot of 5 µL standards or samples was transferred into wells of a clear-bottom 96-well plate, and 200 µL of working reagent was added. The mixture was incubated at room temperature for 3 minutes before measuring the absorbance at 612 nm. The amount of $Ca^{2-}$ present in the samples was determined by calibrating against the linear region of the standard curve. As shown in FIG. 3C, calcium deposition in the bone-like functional subunits was one tenth of that in native cartilage. The calcium deposition in co-cultures increased continually as the time of co-culture increased, suggesting that the osteogenic phenotype is maintained and further supported by the co-culture conditions.

Example 10

SEM and EDX Analysis of the Osteochondral Constructs and Native Osteochondral Plug To examine the microstructure of the tri-layered constructs, samples were processed for scanning electron micrograph (SEM) analysis. The samples were rinsed with phosphate-buffered saline and fixed in 2.5% glutaraldehyde for 2 h at 4° C. After dehydration through a graded series of ethanol, the tri-layered constructs were critical point dried and fractured to expose their cross sections. The samples were mounted onto the holder with carbon resin, and sputter coated with gold-palladium before examination. The samples were then examined with SEM coupled with energy-dispersive X-ray (EDX) spectrometry (LEO 1530; LEO Electron Microscopy, Cambridge, UK) for microstructural analysis (data not shown), and for detection of calcium and phosphorus as well as their relative distribution in the samples. The quantities of these calcium and phosphorus were measured, and the calcium to phosphorus molar ratios calculated (Table 1). The calcium and phosphate content and their molar ratios suggested that the calcium content at the interface is high while that in the uncalcified chondrogenic or cartilage layer is negligible. This again confirms the zonal organization of the osteochondral graft. Moreover, the fiber morphology at the fiber structures of different layers also agree with other histological and biochemical evaluation as many ground substances including GAGs can be found depositing on collagen fiber meshwork in the cartilage layer while many calcium phosphate granules or deposits can be found around collagen fibers in the bone layer. Most importantly, many well aligned collagen bundles or fibers could not be identified in the calcified cartilage interface, which had been characterized by the vertically running collagen fibers.

Example 11

SEM Image Pre-Processing and Analysis for Collagen Fiber Alignment by Radon Transform MATLAB® software was used to correct for the non-uniform illumination and enhance the contrast of the SEM images before further analysis. In brief, grayscale SEM images were first converted to binary images. Skeletonization was then carried out on the binary images before Radon transform. In MATLAB, an image can be regarded as a matrix of intensities. Radon transform is the projection of the image intensity along a radial line oriented at a specific angle $\theta$. $\theta$ was specified to be from 0 to 179 degrees, by the use of Radon transform, 180 values were generated representing the sum of size of the lines that were oriented at that particular angle for each of the 180 angles. An intensity plot at each angle was then generated so that the orientation of fibers could be found.

The variability of the peaks illustrating whether there is preferred alignment is shown in Table 2 below.

TABLE 2

Mean variance with 95% confidence intervals on all or top 50% peaks with intensities above the median value in different layers of the osteochondral graft

| Mean variance (95% C.I.) | Undifferentiated | Chondrogenic | Interface | Osteogenic |
|---|---|---|---|---|
| Top 50% peaks above median | 3552 (464) | 2818 (775) | *437 (328) | 2505 (808) |
| All peaks above median | 3378 (431) | 2906 (587) | *1697 (367) | 2628 (567) |

Results showed that the peak angles varied little in the interface region, suggesting the preferred angle of the fibers or bundles. This further confirms in the scanning electron micrography.

Example 12

BrdU Labeling of rMSCs

In order to track the undifferentiated MSCs during the interface formation, the middle undifferentiated rMSCs-collagen gel layer was labeled with 5-bromo-2-deoxyuridine (BrdU) before combining it with the pre-differentiated layers. The tri-layered constructs were then cultured for 14 days before analysis. Upon completion of the tri-layered culture, the constructs were fixed and BrdU immunohistochemistry was conducted to track whether the interface cells were differentiated from the undifferentiated rMSCs. In brief, sections were incubated with 2N HCl at 37° C. for 30 minutes for antigen retrieval. They were then neutralized with sodium tetraborate solution for 10 minutes. After overnight incubation at 4° C. with a mouse anti-BrdU monoclonal antibody (clone BMC 9318; Roche) at a dilution of 1:1000 in PBS, sections were incubated with an anti-mouse secondary antibody at a dilution of 1:800 in PBS for 30 minutes at room temperature. The Vectastain ABC kit (Vector Laboratories) and the DAB substrate system (Dako) were used for color development in both cases according to the suppliers' instructions. Whether BrdU labeling interacts with the differentiation process has also been investigated by incubating BrdU-labeled MSCs with normal medium for 1, 7 and 21 days or chondrogenic medium for 21 days.

BrdU labeled undifferentiated MSCs could be localized at the interface zone, suggesting that the formation of the hypertrophic chondrocytes at the interface is at least contributed by the undifferentiated MSCs present in the middle layer.

Example 13

Figure 4:
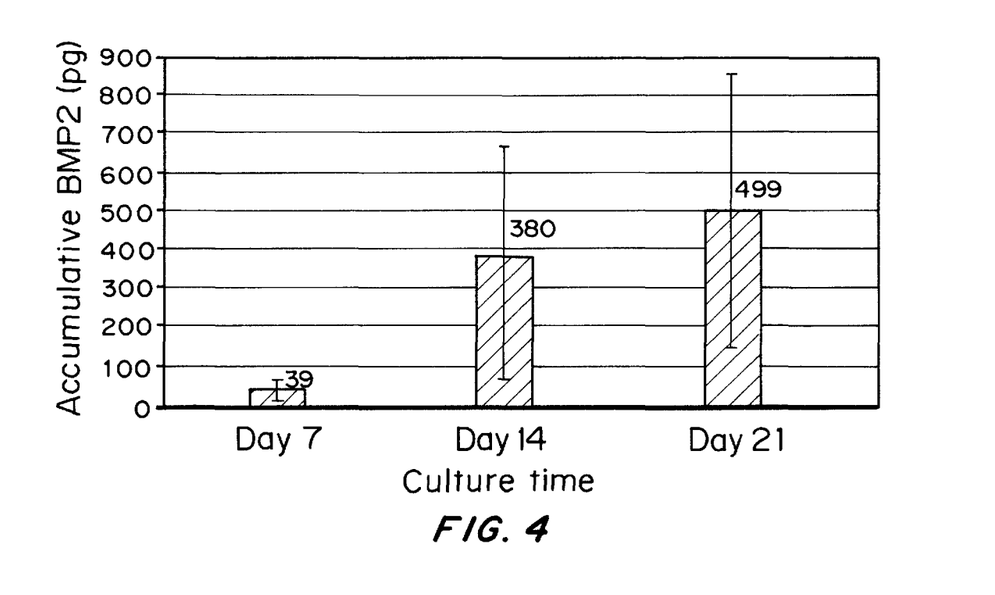
FIG. 4 is a bar graph showing the accumulative amount (pg) of BMP2 secreted from osteogenic differentiated MSC-collagen microspheres as a function of culture time (7, 14, and 21 days).

Secretion of BMP2 From Osteogenic Differentiated Progenies of MSCs in the Bone-Like Functional Subunits Osteogenic functional subunits of different sizes were made as described in Example 5, using mouse MSCs and collagen. Constructs made from 2.5, 10, 50 and 150 µL droplets were made and cultured in osteogenic differentiation medium for 21 days. During these 3 weeks, the conditioned medium from these functional subunits were collected and analyzed for bone morphogenic protein 2 (BMP2) by ELISA. The quantity of BMP2 in the collected media was measured against a calibration curve. The increase in BMP2 secretion over time from bone-like functional subunits of different sizes is shown in FIG. 4. The results show that increasing BMP2 was secreted as culture time increased, suggesting that BMP2 was continuously synthesized and secreted by the osteogenic differentiated progenies of MSCs present in the osteogenic subunits. Since BMP2 is able to stimulate chondrocyte hypertrophy, it is possible that secreted factors including BMP2 from the osteogenic functional subunits (the bottom layer) induce the undifferentiated MSCs in the middle layer to differentiate towards the calcified cartilage phenotype.

Example 14

Osteochondral Repair by Layers of Functional Subunits

In these experiments, skeletally mature New Zealand White rabbits (>5 months old) were used. Bilateral knee joints from the same rabbit were randomly divided into the experimental side and the control side. Upon general anesthesia, a medial parapatellar incision was made on the bilateral knee joint. The dissection was continued until the medial femoral condyle was exposed. Full-thickness osteochondral defects, 4 mm in diameter and 4 mm in depth, were created in the medial femoral condyle using sterile punches. Osteogenic and chondrogenic functional subunits prepared as described above were set aside during the surgery. Multiple osteogenic functional subunits were implanted to press-fit the defect, leaving a thin layer on the top. Multiple chondrogenic functional subunits were then topped on the osteogenic layer, again press-fitting the defect. A spatula was used to press-fit the defect. The implanted construct was localized into the defect by securing with a layer of collagen gel under a photochemically crosslinked collagen membrane, which was fixed by a suture. On the control side, the defect was left empty. Wound closure was performed in layers. The rabbits were allowed free movement after operation. One month post-implantation, the gross appearance of the defect was examined and recorded. Full thickness osteochondral biopsies were taken for fixation and decalcification, and then histological, histochemical and immunohistochemical analyses.

Excellent zonal organization with layers of cartilage zones and the calcified cartilage interface with wavy tide mark separating the chondral and the subchondral bone layers was found. In contrast, natural healing (control discussed above) and defects repaired with undifferentiated or naïve subunits still showed massive fibrous tissue without zonal organizations at all at this time point.

Example 15

Osteochondral Repair by the Tri-Layered Osteochondral Constructs with Proper Zonal Organization Regenerated in Vitro In these experiments, full-thickness osteochondral defects were created in skeletally mature New Zealand White rabbits (>5 months old) as described in Example 14. rMSCs are isolated and cultured as in Examples 1 and 2. The tri-layered osteochondral construct with intact calcified interface and therefore proper zonal organization was prepared using autologous cells and using steps as described in Examples 3-5 and 7 and was implanted to press-fit the defect. An aliquot of collagen gel was applied to the construct surface and a photochemically crosslinked collagen membrane was used to secure the implant with a single suture. Treatment on the control side, other procedures, time for sample harvest and preparation were all the same as stated in Example 14.

Excellent zonal organization with layers of cartilage zones and the calcified cartilage interface with wavy tide mark separating the chondral and the subchondral bone structures. In contrast, natural healing (control discussed above) still showed massive fibrous tissue without zonal organizations at all at this time point.

Example 16

Figure 5:
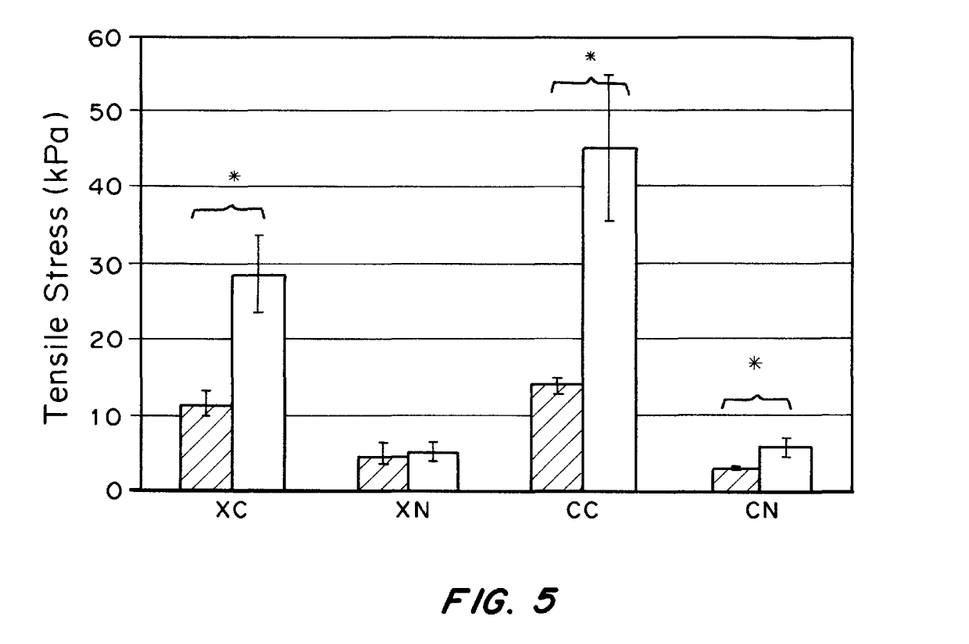
FIG. 5 is a bar graph showing tensile strength (kPa) of bioengineered osteochondral constructs 7 days (solid bars) and 21 days (open bars) after the following conditions: 1) without compression, with chondrogenic medium ("XC"); 2) without compression, with normal growth medium ("XN"); 3) with compression, with chondrogenic medium ("CC"); and 4) with compression, with normal growth medium ("CN"). *p=0.05.

Co-Culture Osteochondral Graft in Compression-Based Bioreactor rMSCs are isolated and cultured as in Examples 1 and 2. Naïve subunits of 704 sizes were fabricated as described in Example 3. Cartilage-like and bone-like functional subunits with cylindrical shape and size of 100 µL were fabricated as described in Examples 4 and 5, respectively, for 21 days. The functional subunits and naïve subunits were combined at the end of 21 days to form the complex tissue with heterogeneous tissue components. These structures were mechanically compressed using a regime of 10% peak-to-peak displacement, 0.5 Hz, and 1 hour per day for 21 days, while culturing in chondrogenic differentiation medium as described in Example 4, using a bioreactor setup. The complex tissue like structures were then processed for histological histochemical and immunohistochemical evaluation as described in Example 8. Histological evaluation of the samples revealed an interface region was positive for GAGs, type II collagen as markers for cartilage and also positive for von kossa staining as a marker for calcification. For all constructs with compression-based bioreactor co-cultures, the interfaces were intact and the whole constructs were stable and manipulable. On the other hand, some constructs which did not expose to the compression-based bioreactor co-culture, could not maintain the integrity and different layers fall apart. Upon conducting tensile strength test on intact constructs surviving the co-culture period, the interfacial strength in those with chondrogenic co-culture medium was much higher than those in normal medium, while in those with compression during the loading period, the interfacial strength is also higher than those without compression particularly in the normal medium and in later time points (FIG. 5).

Example 17

Controlling Cell Alignment Using Torsion-Based Bioreactor rMSCs are isolated and cultured as in Examples 1 and 2. Bone-like subunit of 1000 µl was fabricated as described in Example 5, on a gear-like polycarbonate rod for 21 days. A hollow tube or lamella subunit of 3000 µl was fabricated between two bone-like subunits as described in example 5 using a custom-made container, which consists of a smaller inner cylinder inserting at the center of a large outer cylinder. The lamellar subunit was formed by filling the cell-matrix mixture in the cavity between the outer and the inner cylinder. After removal of the outer cylinder, the complex tissue consisting of the two bone-like subunits and the lamella subunit were mount to the bioreactor and torsion loaded using a regime of 15 degree at 0.5 Hz and 2 hours per day for 14 days while culturing in normal medium using a bioreactor setup. Control structures were exposed to static loading by simply clamping the structures onto the bioreactor. The structures were cultured in normal medium using a bioreactor for the same period of time. The complex tissue structures were then processed for histological evaluation as described in Example 8. A MATLAB based image analysis software was used to evaluate the cell alignment in the construct. Results showed that cells orient to a preferred angle of around 45° in those under cyclic torsion loading while those under static loading (along the long axis of the bioreactor) were of around 100° (Table 3). Multiple lamella can be used to create cell alignment at different preferred angles and such structures are important for tissues such as annulus fibrosus of intervertebral disc.

TABLE 3

Cell alignment under static loading and cyclic torsion loading

| N = 3 | Mean | SD |
| --- | --- | --- |
| Static | 107.33° | 4.93° |
| Dynamic | 47.67° | 12.50° |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. Method comprises:
   (a) combining
      (i) a first layer of differentiated functional subunits that consists of microencapsulated mesenchymal stem cells induced into osteogenic differentiation,
      (ii) a second layer of undifferentiated subunits that consists of of microencapsulated mesenchymal stem cells, and
      (iii) a third layer of differentiated functional subunits that consists of microencapsulated mesenchymal stem cells induced into chondrogenic differentiation,
   wherein the second layer is adjacent to the first layer and separates the first and third layer, and the third layer is adjacent to the second layer; and
   (b) culturing in vitro the combined first, second and third layers in a chondrogenic differentiation medium to form a bioengineered osteochondral tissue graft that mimics the structural and functional characteristics of a complex tissue,
   wherein said culturing induces the microencapsulated mesenchymal stem cells in the second layer to form a calcified zone between the first and the third layers.

2. The method of claim 1, wherein the microencapsulated mesenchymal stem cells are microencapsulated in an extracellular matrix biomaterial.

3. The method of claim 2, wherein the extracellular matrix biomaterial is selected from the group consisting of collagen, fibrin, hyaluronic acid, and glycosaminoglycan.

4. The method of claim 1, wherein the differentiated and undifferentiated functional subunits have a structure selected from the group consisting of a microsphere, a cube, a ring, and a micro-rod.

5. The method of claim 1, wherein the chondrogenic differentiation medium comprises TGF-β1.

6. The method of claim 1, wherein said culturing is in the presence of a force selected from the group consisting of torsion, compression, tension, and a combination thereof.

7. The method of claim 1, further comprising fine-tuning the structural and functional properties of the bioengineered osteochondral tissue graft by exposing it to suitable biological, chemical, or physical co-culture conditions.

8. The method of claim 1, wherein the undifferentiated subunits are tissue micromasses.

9. The method of claim 8, wherein the tissue micromasses have a volume of $10^{-6}$ ml.

10. The method of claim 8, wherein the tissue micromasses have from 100 to 1000 cells.

11. The method of claim 7, wherein the biological co-culture conditions are selected from the group consisting of conditioned medium, growth factors, cytokines, serum, and a combination thereof.

12. The method of claim 7, wherein the chemical co-culture conditions are selected from the group consisting of antioxidants, acids, alkali, oxygen tension, and a combination thereof.

13. The method of claim 7, wherein the physical co-culture conditions are selected from the group consisting of torsion, compression, tension, and a combination thereof.

14. The method of claim 1, wherein the microencapsulated mesenchymal stem cells are microencapsulated in collagen.

15. The method of claim 1, wherein the microencapsulated mesenchymal stem cells are from a cell-matrix mixture having a cell density of about $5 \times 10^5$ cells/ml.

16. The method of claim 1, wherein the microencapsulated mesenchymal stem cells are microencapsulated bone marrow derived mesenchymal stem cells or microencapsulated adipose tissue derived mesenchymal stem cells.

17. A bioengineered osteochondral tissue graft produced by the method of claim 1.

* * * * *

UNITED STATES PATENT AND TRADEMARK OFFICE
CERTIFICATE OF CORRECTION

| | |
|---|---|
| PATENT NO. | : 11,786,636 B2 |
| APPLICATION NO. | : 13/159837 |
| DATED | : October 17, 2023 |
| INVENTOR(S) | : Barbara Pui Chan et al. |

It is certified that error appears in the above-identified patent and that said Letters Patent is hereby corrected as shown below:

In the Claims

Claim 1, Column 19, Line 42, replace "Method comprises" with --A method of making a bioengineered osteochondral tissue graft, the method comprises:--.

Claim 1, Column 19, Line 56, replace "in vitro" with --*in-vitro*--.

Signed and Sealed this
Second Day of January, 2024

Katherine Kelly Vidal
*Director of the United States Patent and Trademark Office*